(12) United States Patent
Lim et al.

(10) Patent No.: US 7,828,828 B2
(45) Date of Patent: Nov. 9, 2010

(54) INTERVERTEBRAL JOINT

(75) Inventors: Roy Lim, Germantown, TN (US); Michael MacMillan, Winter Park, FL (US)

(73) Assignee: Warsaw Orthopedic, Inc, Warsaw, IN (US)

( * ) Notice: Subject to any disclaimer, the term of this patent is extended or adjusted under 35 U.S.C. 154(b) by 780 days.

(21) Appl. No.: 11/105,836

(22) Filed: Apr. 14, 2005

(65) Prior Publication Data
US 2006/0235414 A1   Oct. 19, 2006

(51) Int. Cl.
   A61B 17/04   (2006.01)
   A61B 17/84   (2006.01)
   A61B 17/86   (2006.01)

(52) U.S. Cl. .................. 606/300; 606/304; 606/305

(58) Field of Classification Search .............. 606/61, 606/70–73, 300, 301, 304, 305, 307, 308, 606/323, 287, 90, 105, 279; 623/13.11–13.14, 623/20.22, 17.14, 22.36, 17.11–17.16, 18.11, 623/19.11, 19.12, 20.11, 20.14, 21.13, 21.16, 623/21.17, 22.11, 22.15, 22.21–22.4; 433/172–175; 411/380, 383, 395, 403, 479; 403/56, 76, 403/77, 90, 114, 122, 127
See application file for complete search history.

(56) References Cited

U.S. PATENT DOCUMENTS

| | | | | |
|---|---|---|---|---|
| 3,808,606 A * | 5/1974 | Tronzo | ................ | 428/613 |
| 4,792,337 A * | 12/1988 | Muller | ................ | 623/22.36 |
| 4,840,632 A * | 6/1989 | Kampner | ................ | 623/22.36 |
| 4,950,270 A | 8/1990 | Bowman et al. | | |
| 5,151,104 A * | 9/1992 | Kenna | ................ | 606/73 |
| 5,203,657 A * | 4/1993 | Nagoshi et al. | ................ | 411/399 |
| 5,242,444 A | 9/1993 | MacMillan | | |
| 5,258,031 A | 11/1993 | Salib et al. | | |
| 5,314,488 A * | 5/1994 | Hayashi et al. | ................ | 623/22.36 |
| 5,507,816 A | 4/1996 | Bullivant | | |
| 5,827,285 A | 10/1998 | Bramlet | | |
| 5,993,486 A * | 11/1999 | Tomatsu | ................ | 623/13.11 |
| 6,019,759 A * | 2/2000 | Rogozinski | ................ | 606/308 |
| 6,099,571 A * | 8/2000 | Knapp | ................ | 623/21.16 |
| 6,162,257 A * | 12/2000 | Gustilo et al. | ................ | 623/22.32 |
| 6,187,008 B1 | 2/2001 | Hamman | | |
| 6,197,028 B1 | 3/2001 | Ray et al. | | |
| 6,228,121 B1 * | 5/2001 | Khalili | ................ | 623/22.36 |
| 6,267,765 B1 * | 7/2001 | Taylor et al. | ................ | 606/61 |
| 6,375,684 B1 * | 4/2002 | Kriek | ................ | 623/23.39 |
| 6,503,281 B1 * | 1/2003 | Mallory | ................ | 623/22.15 |
| 6,517,543 B1 * | 2/2003 | Berrevoets et al. | ................ | 606/73 |
| 6,635,059 B2 * | 10/2003 | Randall et al. | ................ | 606/916 |
| 6,733,502 B2 * | 5/2004 | Altarac et al. | ................ | 606/61 |
| 6,808,526 B1 | 10/2004 | Magerl et al. | | |
| 6,921,403 B2 | 7/2005 | Cragg et al. | | |
| 2002/0038123 A1 | 3/2002 | Visotsky et al. | | |

(Continued)

FOREIGN PATENT DOCUMENTS

DE    19755369 A1    6/1998

(Continued)

*Primary Examiner*—Eduardo C Robert
*Assistant Examiner*—Tara R Carter

(57) ABSTRACT

An intervertebral joint with one embodiment comprising a socket screw, a ball screw, and two support screws. The socket screw and ball screw form a socket joint between two vertebral members. A first support screw braces the socket screw. A second support screw braces the ball screw.

11 Claims, 12 Drawing Sheets

U.S. PATENT DOCUMENTS

| | | |
|---|---|---|
| 2002/0087161 A1 | 7/2002 | Randall et al. |
| 2002/0198527 A1 | 12/2002 | Muckter |
| 2003/0065332 A1 | 4/2003 | TenHuisen et al. |
| 2004/0015172 A1 | 1/2004 | Biedermann et al. |
| 2004/0122431 A1 | 6/2004 | Biedermann et al. |
| 2004/0143267 A1 | 7/2004 | Fallin |
| 2005/0033434 A1* | 2/2005 | Berry .................. 623/17.14 |
| 2005/0113919 A1 | 5/2005 | Cragg et al. |
| 2005/0113929 A1 | 5/2005 | Cragg et al. |
| 2005/0234454 A1* | 10/2005 | Chin ....................... 606/61 |
| 2006/0058800 A1 | 3/2006 | Ainsworth et al. |
| 2006/0079898 A1 | 4/2006 | Ainsworth et al. |
| 2006/0173461 A1* | 8/2006 | Kay et al. ................ 606/73 |
| 2006/0190079 A1 | 8/2006 | Istephanous et al. |
| 2006/0259147 A1 | 11/2006 | Krishna et al. |

FOREIGN PATENT DOCUMENTS

| | | |
|---|---|---|
| GB | 2370619 | 7/2002 |
| WO | WO 94/26190 | 11/1994 |
| WO | 2004064692 A2 | 8/2004 |

* cited by examiner ns. The screws 20, 30, 40 and 50 can be made of titanium, stainless steel, cobalt chrome, other metals, plastics, bioabsorbable material, or a combination thereof. The screws 20, 30, 40 and 50 may comprise unitary members, or may have a multi-piece construction. The screws 20, 30, 40 and 50 may be self-tapping or self-threading. The particular embodiment illustrated is used as a lumbosacral joint between the L5 lumbar vertebra 12 and the S1 sacral vertebra 14. Those skilled in the art will recognize that the intervertebral joint 10 may be used between other vertebral members in the spinal column, and could also be adapted for use in other parts of the body.

INTERVERTEBRAL JOINT

BACKGROUND

One cause of persistent lower back pain is degeneration of the intervertebral disc connecting the L5 lumbar vertebra and S1 sacral vertebra. Removal of the degenerated disc followed by spinal fusion is common procedure to alleviate the lower back pain. Spinal fusion typically results in some loss of mobility. Therefore, alternative treatments and procedures to stabilize the lumbosacral joint while preserving some mobility is desirable.

SUMMARY

The present invention is directed to embodiments of an intervertebral joint and methods of mounting and using the joint. In one embodiment, the intervertebral joint comprises a socket screw, a ball screw and two support screws. The socket screw may include a ball socket and an angularly disposed shaft. The socket screw may be inserted at an angle into a superior vertebra. A first support screw may be inserted at an angle into the superior vertebra engages and supports the socket screw. The ball screw may comprise a spherical head that mates with the ball socket on the socket screw and a threaded shaft. A lateral socket may be formed in the shaft of the ball screw adjacent the spherical head. The ball screw may be inserted at an angle into an inferior vertebra and engages with the ball socket on the socket screw. A second support screw may be inserted at an angle in the inferior vertebra to engage the lateral socket in the ball screw and provide support for the ball screw.

DETAILED DESCRIPTION

Figure 1:
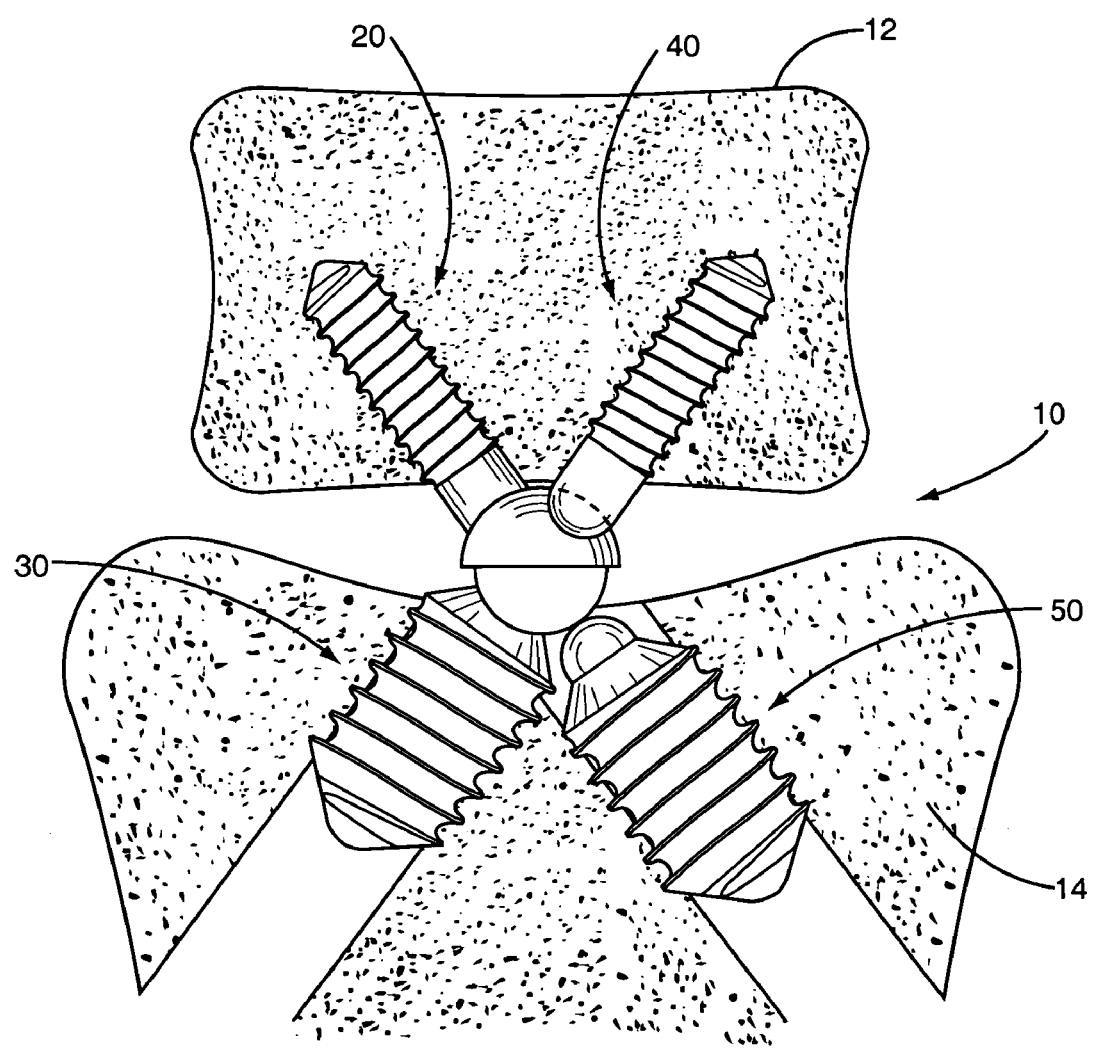
FIG. 1 illustrates a first exemplary intervertebral joint according to one embodiment of the present invention.

Referring now to the drawings, FIG. 1 illustrates one exemplary embodiment of an intervertebral joint indicated generally by reference numeral 10. The intervertebral joint 10 comprises a socket screw 20, a ball screw 30, and two support screws indicated by reference numerals 40 and 50 respectively. The screws 20, 30, 40 and 50 can be made of titanium, stainless steel, cobalt chrome, other metals, plastics, bioabsorbable material, or a combination thereof. The screws 20, 30, 40 and 50 may comprise unitary members, or may have a multi-piece construction. The screws 20, 30, 40 and 50 may be self-tapping or self-threading. The particular embodiment illustrated is used as a lumbosacral joint between the L5 lumbar vertebra 12 and the S1 sacral vertebra 14. Those skilled in the art will recognize that the intervertebral joint 10 may be used between other vertebral members in the spinal column, and could also be adapted for use in other parts of the body.

Figure 2:
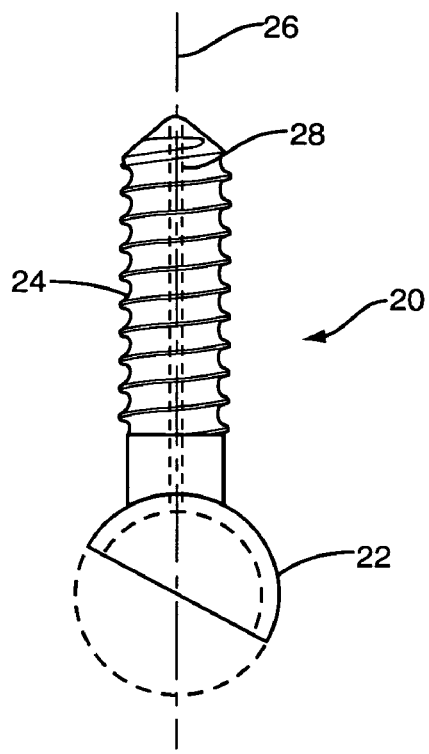
FIG. 2 illustrates a socket screw for the intervertebral joint according to one embodiment of the present invention.

FIG. 2 illustrates the socket screw 20. The socket screw 20 includes a ball socket 22 and a threaded shaft 24. In one embodiment, the ball socket 22 and threaded shaft 24 may comprise one unitary member made of titanium, cobalt chrome, other metal, or plastic. In other embodiments, the ball socket 22 and threaded shaft 24 may be made of different materials. For example, the socket screw 20 may have a titanium shaft 24 with a cobalt chrome ball socket 22. In another example, the socket screw 20 may have a shaft 24 made of a bio-absorbable material to promote bone in-growth with a cobalt chrome or titanium ball socket 22. In the exemplary embodiment, the ball socket 22 has an inner spherical surface with a diameter in the range of approximately 8 mm, and an outer surface with a diameter in the range of approximately 12 mm. The threaded shaft 24 is approximately 6 mm in diameter. The ball socket 22 is disposed at an angle relative to a central axis 26 of the shaft 24. In the exemplary embodiment illustrated, the angle is approximately 45 +/–10 degrees. The socket screw 20 may include a longitudinally extending guide hole 28 for a guide wire.

Figure 3:
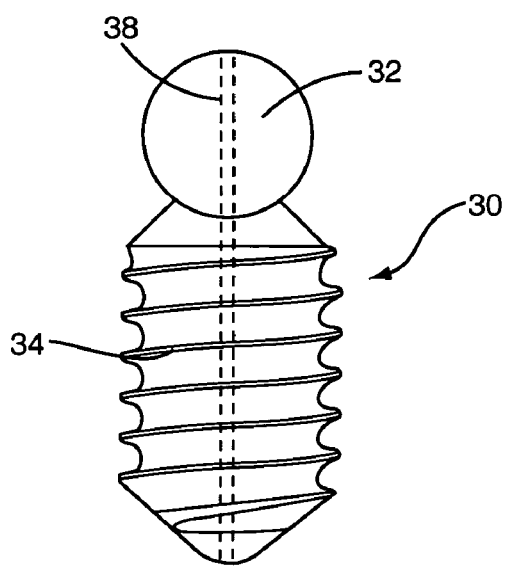
FIG. 3 illustrates a ball socket for the intervertebral joint according to one embodiment of the present invention.

FIG. 3 illustrates the ball screw 30. The ball screw 30 comprises a spherical head 32 and a threaded shaft 34. In one embodiment, the head 32 and threaded shaft 34 may comprise one unitary member made of titanium, cobalt chrome, other metal, or plastic. In other embodiments, the head 32 and threaded shaft 34 may be made of different materials. For example, the ball screw 30 may have a titanium shaft 34 with a cobalt chrome head 32. In another example, the ball screw 30 may have a shaft 34 made of a bio-absorbable material to promote bone in-growth with a cobalt chrome or titanium head 32. The diameter of the spherical head 32 matches the inner surface of the ball socket 22, which is approximately 8 mm in the exemplary embodiment. The diameter of the threaded shaft 34 in the exemplary embodiment is approximately 14 mm. The ball screw 20 may include a longitudinally extending guide hole 38 for a guide wire.

Figure 4:
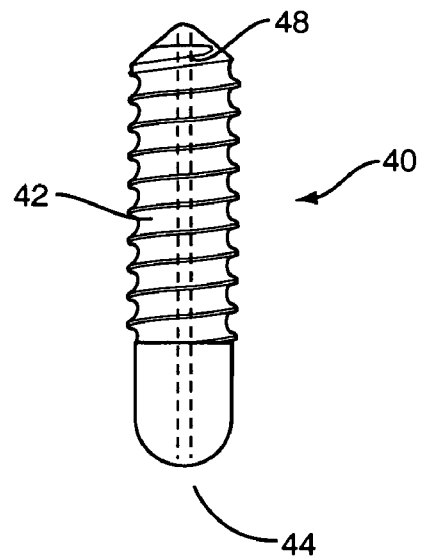
FIG. 4 illustrates a first support screw for the intervertebral joint according to one embodiment of the present invention.

FIG. 4 illustrates a first support screw 40 for engaging and supporting the socket screw 20. Support screw 40 comprises a threaded shaft 42 having a seat 44 formed in one end to engage the socket screw 20. As previously described, the support screw 40 may be a unitary piece, or may be made of two or more different materials. Seat 44 comprises a concave surface in the end of the shaft 42. In the exemplary embodiment, the seat 44 has a generally spherical shape that conforms to the outer surface of the ball socket 22. In other embodiments, the seat 44 may be shaped to conform to the shaft 24 of the socket screw 20. The diameter of the support screw 40 in one embodiment is approximately 6 mm. The support screw 40 may include a longitudinally extending guide hole 48 for a guide wire.

Figure 5:
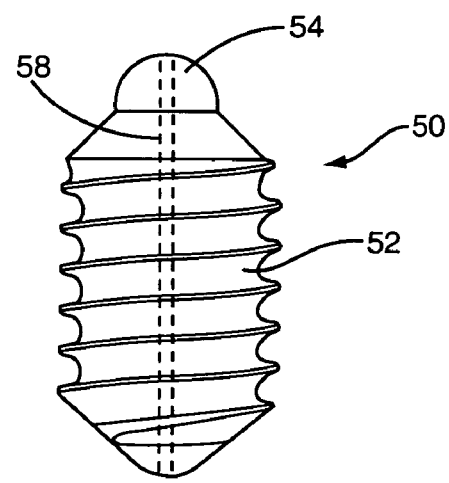
FIG. 5 illustrates a second support screw for the intervertebral joint according to one embodiment of the present invention.

FIG. 5 illustrates a second support screw 50 for engaging and supporting the ball screw 30. Support screw 50 comprises a threaded shaft 52 with a spherical end 54 adapted to contact the head 32 of the ball screw. As previously described, the support screw 40 may be a unitary piece, or may be made of two or more different materials. The diameter of the support screw 50 in the exemplary embodiment is approximately 14 mm. The support screw 50 may include a longitudinally extending guide hole 58 for a guide wire.

FIGS. 6A-6D illustrate a procedure for inserting the intervertebral joint 10. Prior to the insertion of the intervertebral joint 10, a discectomy may be performed to remove all or part of the intervertebral disc. Following the discectomy, approach holes 102 and 104 are drilled in the body of the sacrum 14 through which the socket screw 20 and support screw 40 will be inserted. Approach hole 102 is sized to allow support screw 40 to pass freely through the approach hole 20, but slightly smaller than the shank of the ball screw 30. Approach hole 104 is sized to allow the socket screw 20 to pass through the approach hole 104, but slightly smaller than the shaft 52 of the support screw 50. Guide holes 106 and 108 are then drilled into the body of the L5 lumbar vertebra 12 for the socket screw 20 and support screw 40 respectively. Guide hole 106 is slightly smaller than the shaft 24 of the socket screw 20, while guide hole 108 is slightly smaller than the shaft 42 of support screw 40. A jig or other fixture can be used to drill the approach holes 102, 104 and guide holes 106, 108. Guide hole 106 is axially aligned with approach hole 104, while guide hole 108 is axially aligned with approach hole 102.

Figure 6A:
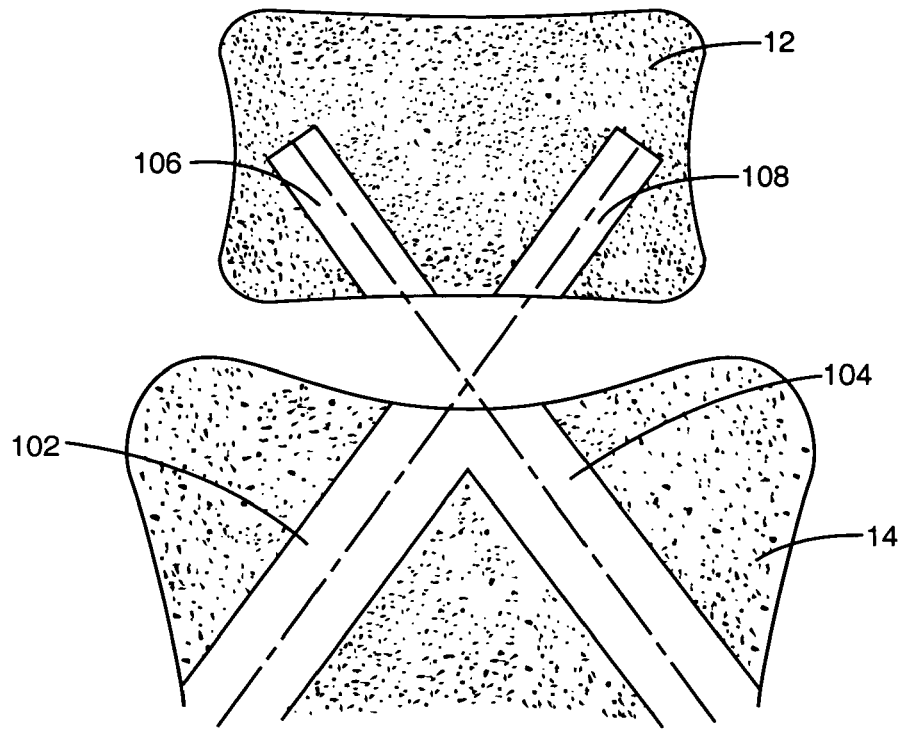
FIGS. 6A-6D illustrate a procedure for inserting the intervertebral joint of FIG. 1 between the L5 lumbar vertebra and the S1 sacral vertebra according to one embodiment of the present invention.
Figure 6B:
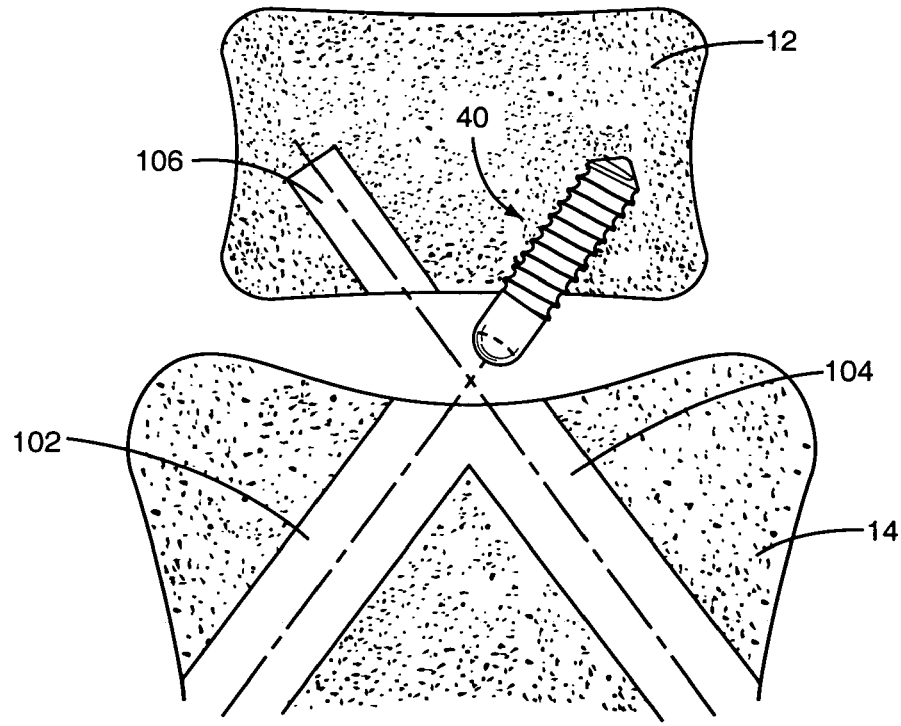
Figure 6C:
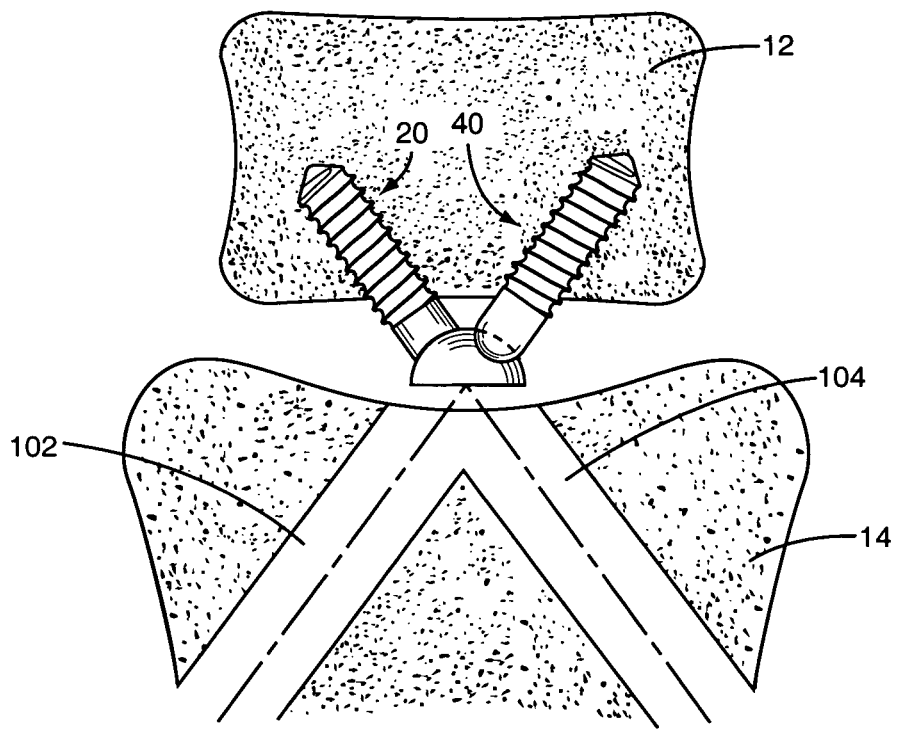
Figure 6D:
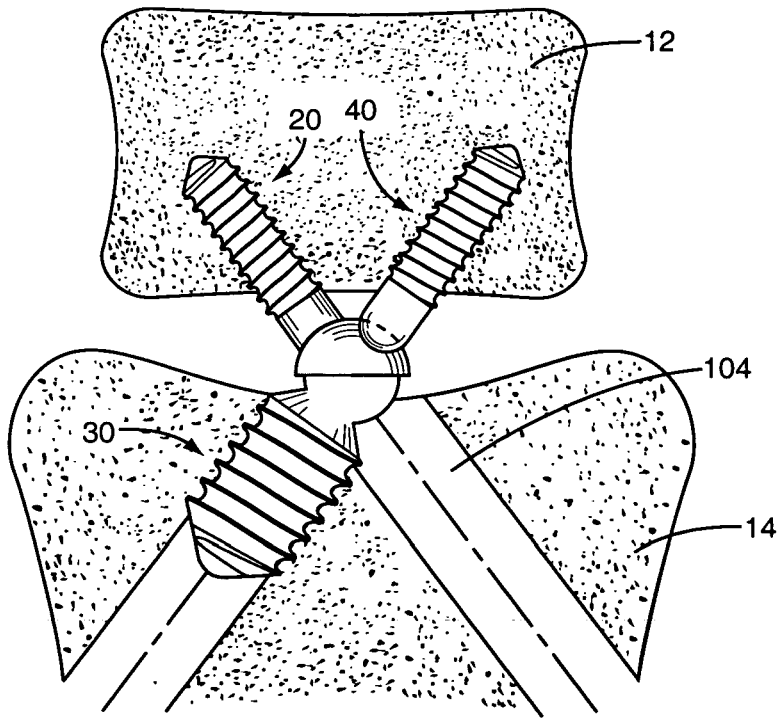

The support screw 40 is inserted through approach hole 102 and threaded into the guide hole 108 as shown in FIG. 6B. The socket screw 20 is then inserted through the approach hole 104 and threaded into the guide hole 106 until the outer surface of the ball socket 22 comes into contact with the seat 44 on the end of the support screw 40 as shown in FIG. 6C. As previously described the support screw 40 and socket screw 20 may be self-threading or self-tapping. A guide wire may be used to guide the support screw 40 and socket screw 20 during insertion. The ball screw 30 is inserted following the socket screw 20 by threading the ball screw 30 into the approach hole 102 until the spherical head 32 seats within the ball socket 22 of the socket screw 20 as shown in FIG. 6D. The intervertebral joint 10 is completed by threading the support screw 50 into the approach hole 104 until the spherical end 54 engages the head 32 of the ball screw 30 as shown in FIG. 1.

Figure 7:
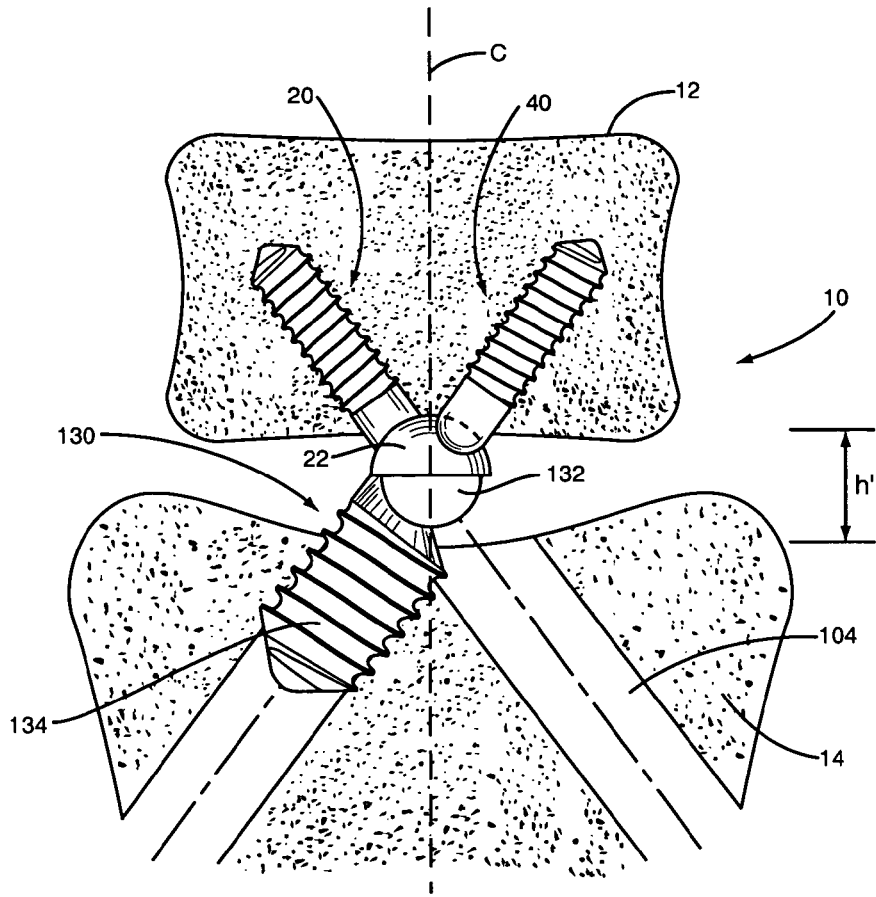
FIG. 7 illustrates a second exemplary intervertebral joint according to one embodiment of the present invention.

FIG. 7 illustrates a second exemplary embodiment of the intervertebral joint 10. This embodiment may be used to distract or separate two vertebral members. This embodiment is similar to the first embodiment and therefore the same reference numerals are used to indicate similar components.

Figure 8:
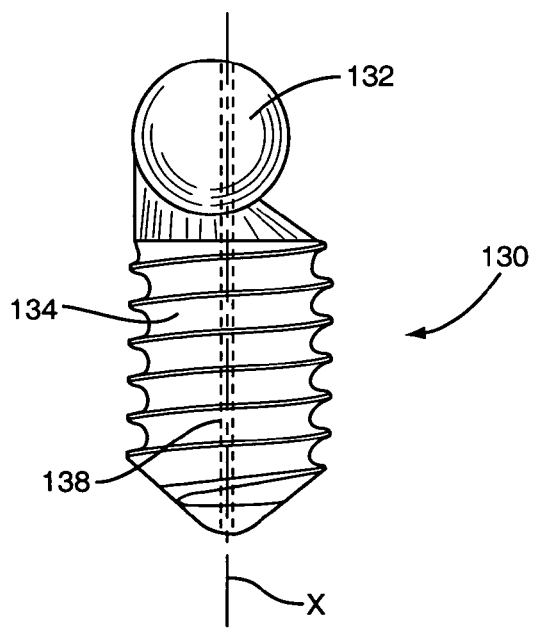
FIG. 8 illustrates a modified ball screw for the intervertebral joint of FIG. 7.

The intervertebral joint shown in FIG. 7 comprises a socket screw 20 and a support screw 40 as previously described. The ball screw 130, however, is modified as illustrated in FIG. 8. The ball screw 130 in this embodiment includes a rounded head 132 and shaft 134. The shaft 134 is centered about a centerline X, with the head 132 being offset from the centerline X. The ball screw may further include a guide hole 138 for a guide wire.

Figure 9A:
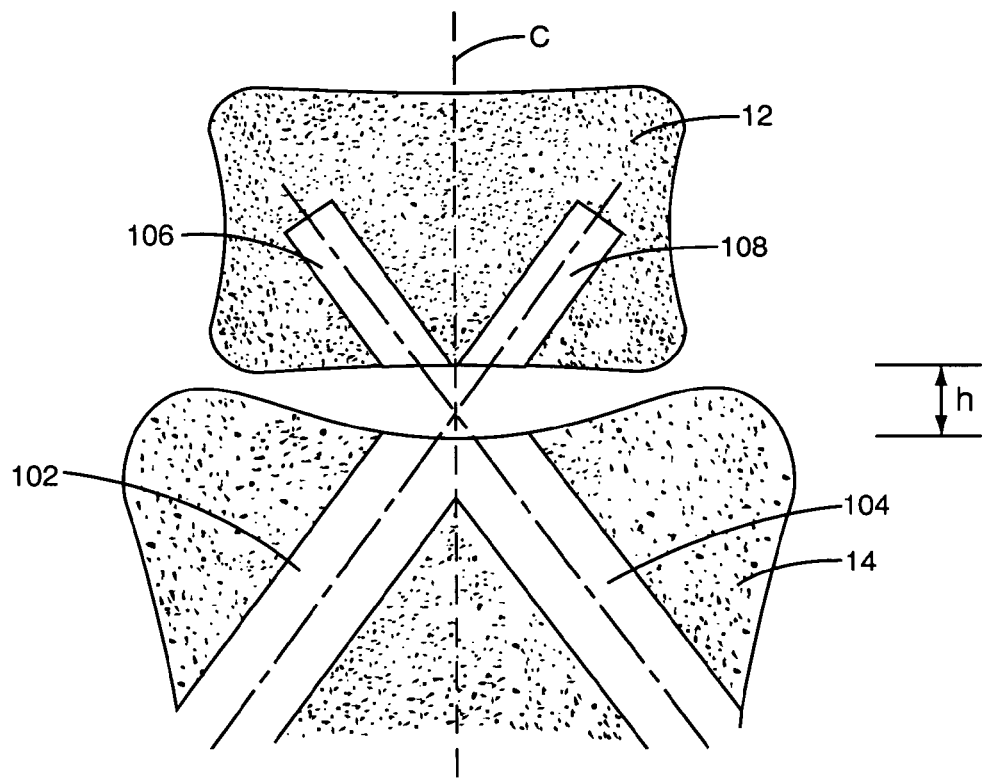
FIGS. 9A-9C illustrate a procedure for inserting the intervertebral joint of FIG. 7 between the L5 lumbar vertebra and the S1 sacral vertebra according to one embodiment of the present invention.
Figure 9B:
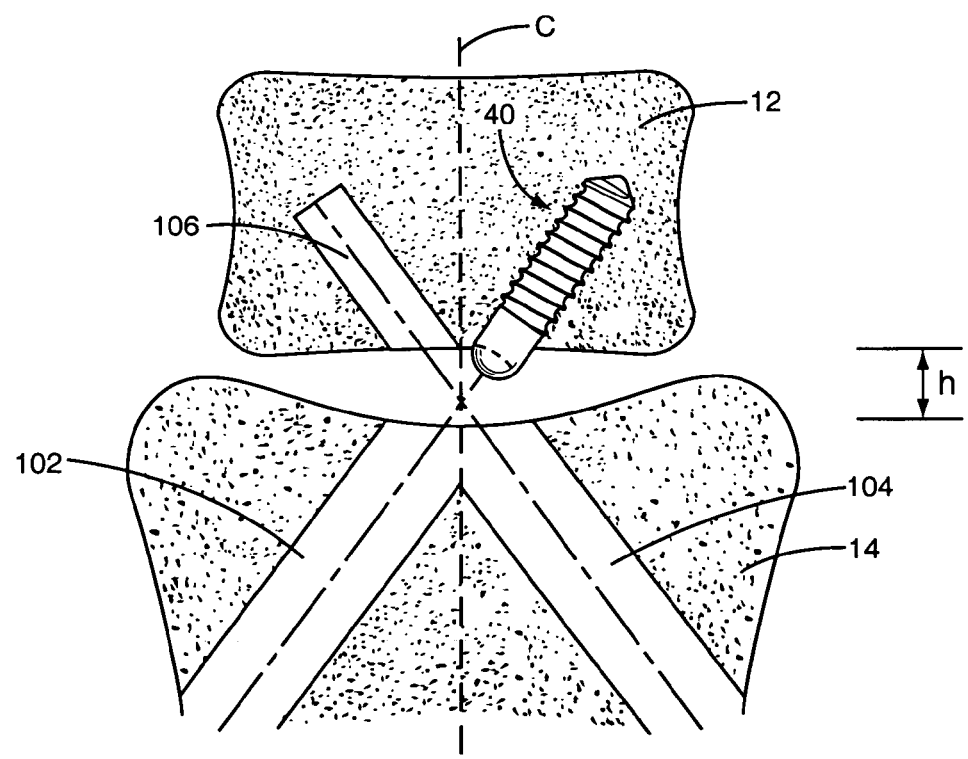
Figure 9C:
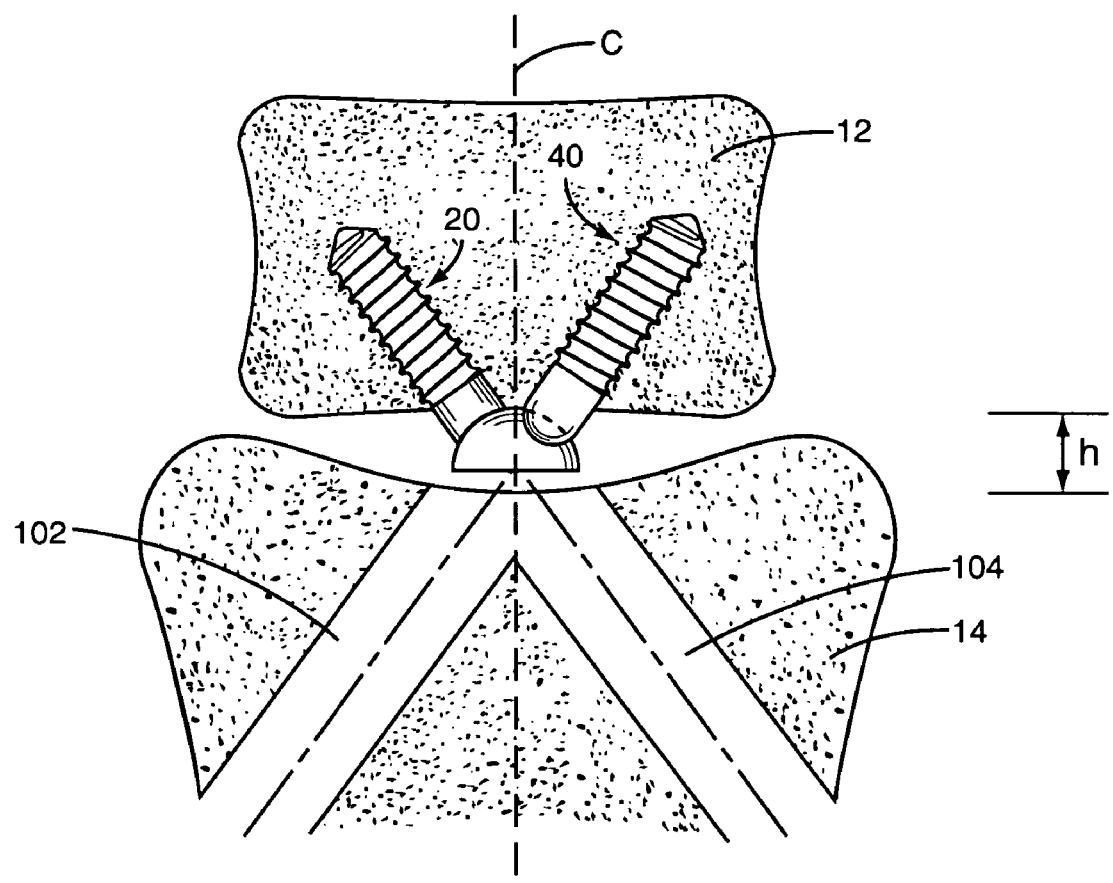

FIGS. 9A-9C illustrate a procedure for inserting the intervertebral joint 10 shown in FIG. 7. Prior to the insertion of the intervertebral joint 10, a discectomy may be performed to remove all or part of the intervertebral disc. At this point, the disc height between the sacrum 14 and lumbar vertebra 12 is h. Following the discectomy, approach holes 102 and 104 are drilled in the body of the sacrum 14, and guide holes 106 and 108 are drilled into the body of the L5 lumbar vertebra 12 as previously described. At this point, the guide holes 106, 108 are co-axially aligned with corresponding approach holes 102 and 104. Support screw 40 is inserted through approach hole 102 and threaded into the guide hole 108 in the lumbar vertebra 12 as shown in FIG. 9B. The socket screw 20 is inserted through approach hole 104 and threaded into guide hole 106 as shown in FIG. 9C. The ball screw 130 is threaded into the approach hole 102 until the head 132 makes contact with the ball socket 22 of the socket screw 20. Further rotation of the ball screw 130 distracts the disc space to h' while maintaining the lumbar vertebra 12 and sacrum 14 aligned on the centerline C.

Figure 10A:
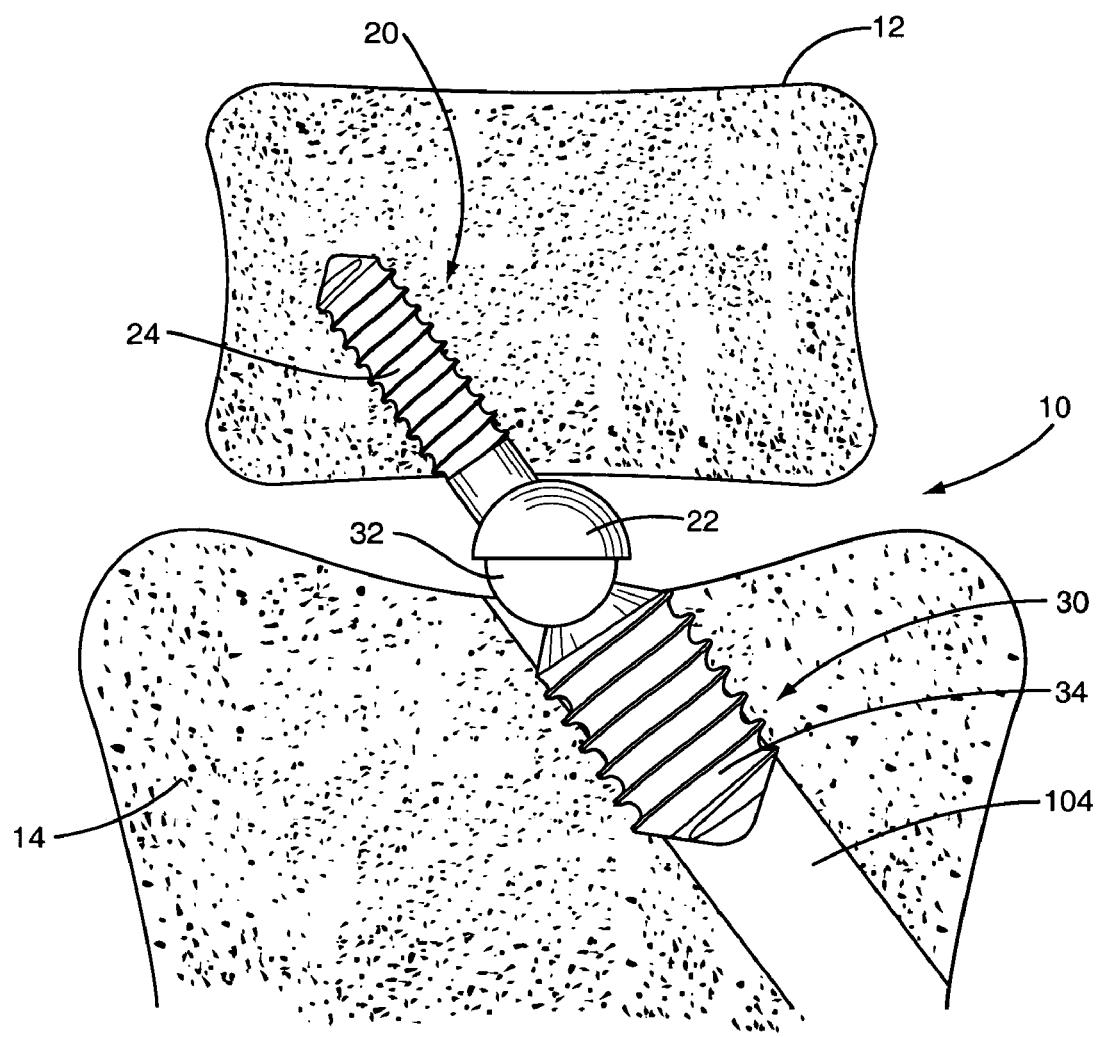
FIGS. 10A and 10B illustrate a third exemplary embodiment of the intervertebral joint having only a socket screw and a ball screw.
Figure 10B:
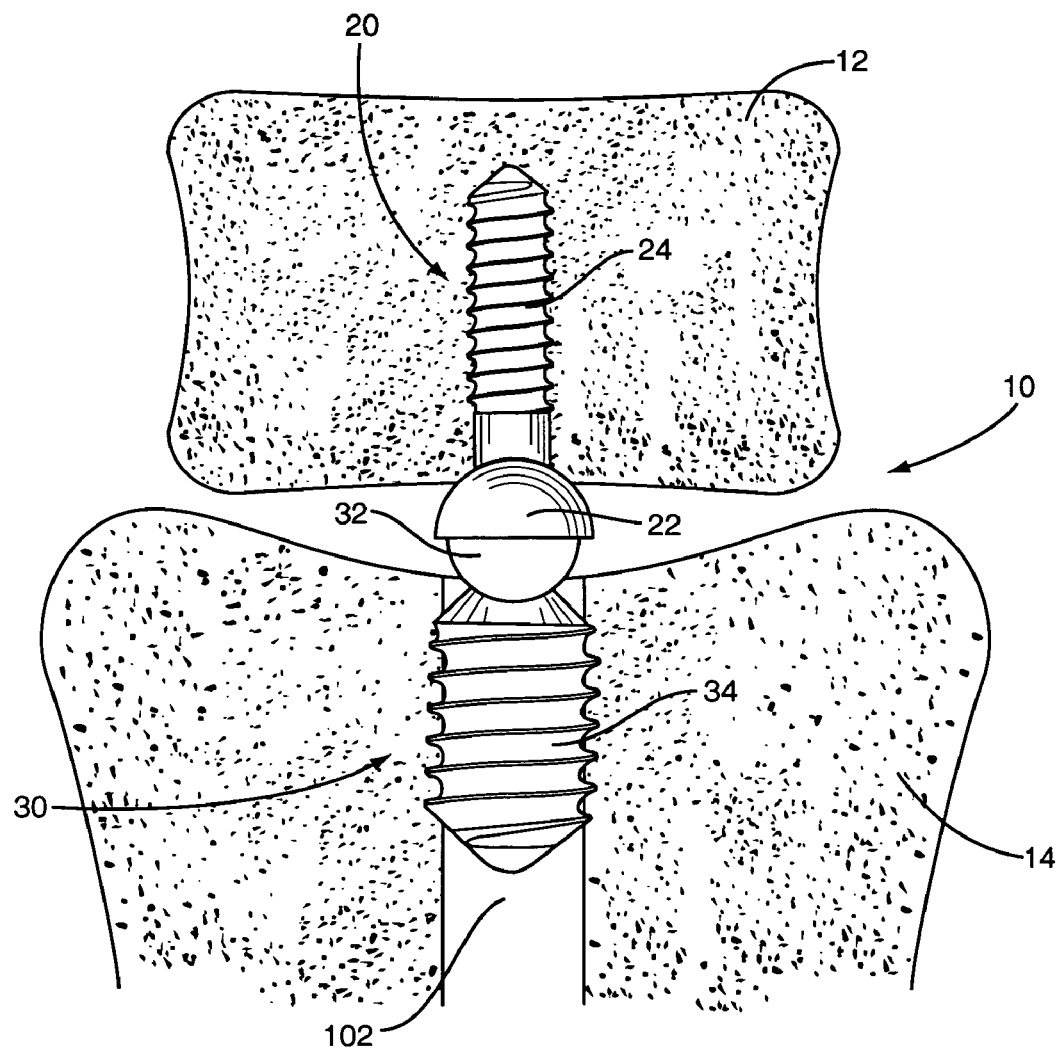

FIGS. 10A and 10B illustrate two variations of a third embodiment of the intervertebral joint 10 comprising only a socket screw 20 and ball screw 30. The socket screw 20 includes a ball socket 22 and threaded shaft 24. In the variation shown in FIG. 1A, the socket screw 20 is the same shown in FIG. 2. In the embodiment shown in FIG. 10B, the ball socket 22 is not tilted but, instead, is aligned with the axis of the threaded shaft 24. The ball screw 30 in both FIGS. 10A and 10B includes a rounded head 32 and threaded shaft 34 as shown in FIG. 3. The diameter of the threaded shaft 34 is slightly larger than the outer diameter of the ball socket 22. The intervertebral joint 10 is inserted by drilling an approach hole 102 in the sacrum 14. The socket screw 20 is then inserted through the approach hole 102 and screwed into the lumbar vertebra 12. The ball screw 30 is threaded into the approach hole 102 until the head 32 seats within the ball socket 22 of the socket screw 20 as shown in FIG. 10. If necessary, the physician may continue to thread the ball screw 30 into the approach hole 102 after contact is made with the ball socket 22 in order to separate the lumbar vertebra 12 and sacrum 14.

Figure 11:
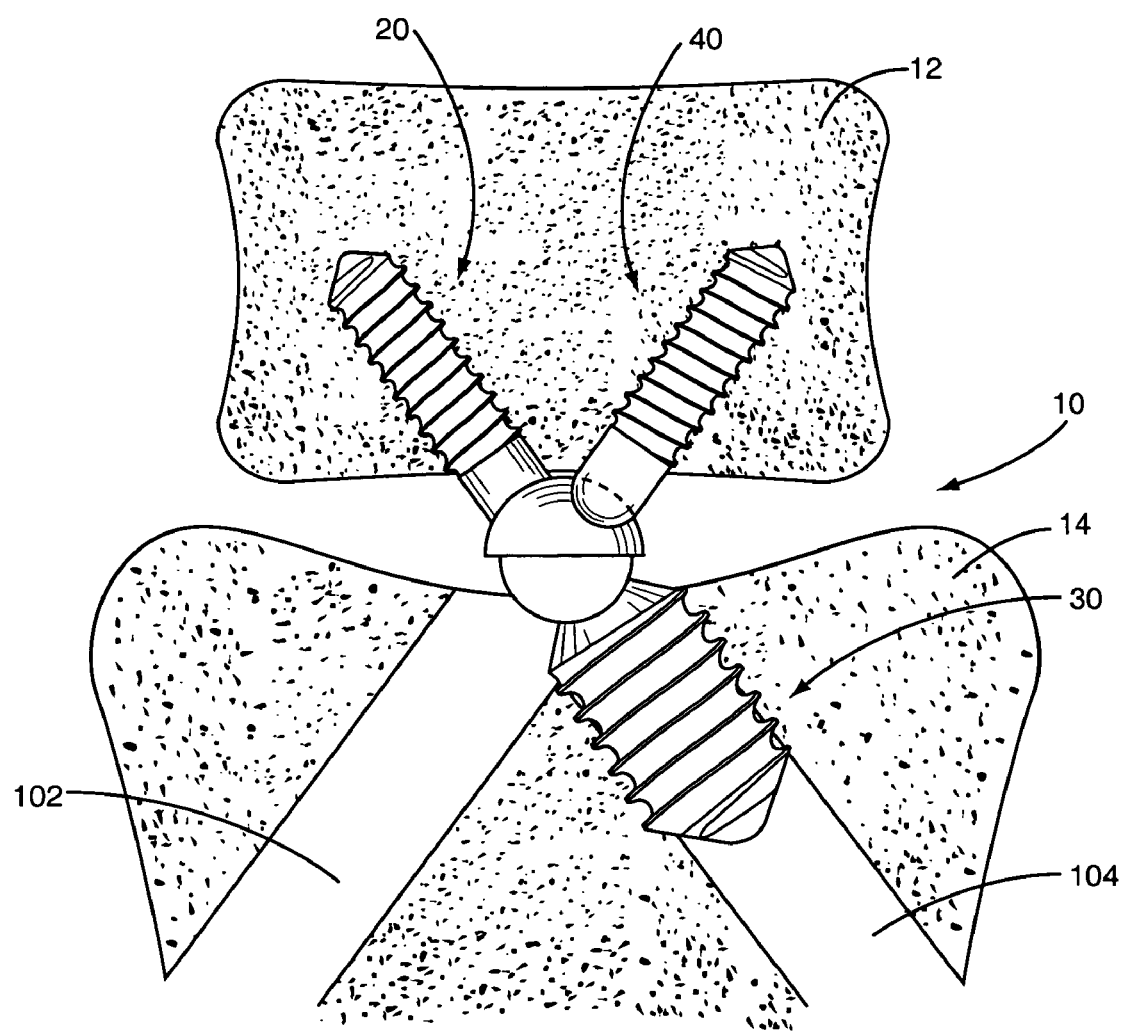
FIG. 11 illustrates a fourth exemplary embodiment of the intervertebral joint having a socket screw, a ball screw and one support screw.

FIG. 11 illustrates a fourth exemplary embodiment of the intervertebral joint having a socket screw 20, a ball screw 30 and one support screw 40 as shown in FIGS. 2-4. In this embodiment, the socket screw 20 and ball screw 30 are coaxially aligned. The support screw 40 is inserted first through an approach hole 102 in the sacrum 14 and threaded into a guide hole 108 in the lumbar vertebra 12 as shown in FIG. 6B. The socket screw 20 is then inserted through approach hole 104 and threaded into a guide hole 106 as shown in FIG. 6C. Finally, the ball screw 30 is threaded into the approach hole 104 until it engages the socket 22 in the socket screw 20 as shown in FIG. 11.

Figure 12:
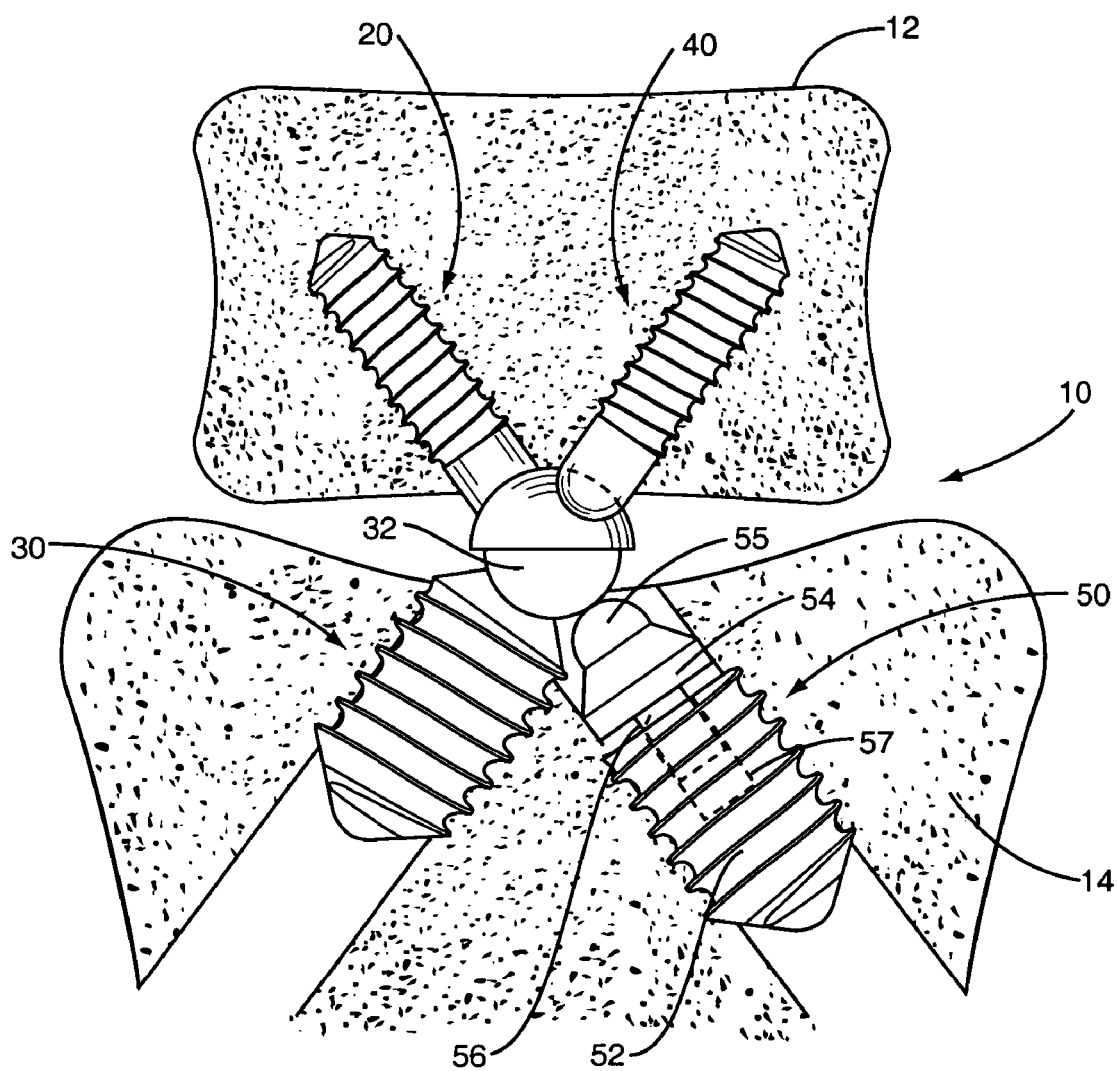
FIG. 12 illustrates a fifth exemplary embodiment of the intervertebral joint.

FIG. 12 illustrates a fifth embodiment of the intervertebral joint 10. This embodiment is similar to the embodiment shown in FIG. 1 and therefore the same reference numerals are used to indicate similar parts. The intervertebral joint 10 shown in FIG. 12 comprises a socket screw 20, ball screw 30, support screw 40, and support screw 50. The socket screw 20, ball screw 30, and support screw 40 are the same as shown in FIGS. 2-4. The support screw 50 comprises an end portion 54 and a threaded shaft 52. The end portion 54 is mounted to the threaded shaft 52 in a manner that allows relative rotation between the end portion 54 and threaded shaft 52. For example, the end portion 54 may include a shaft 56 that extends into an axial bore 57 in the threaded shaft 52. The end portion 54 has a concave ball seat 55 formed therein that is shaped to conform to the outer surface of the ball 32 on the ball screw 30. The procedure for inserting the intervertebral joint 10 is the same as shown in FIGS. 6A-6D. During insertion of the support screw 50, the threaded shaft 52 can be rotated after the concave seat 55 makes contact with the ball 32 on the ball screw 30.

Figure 13:
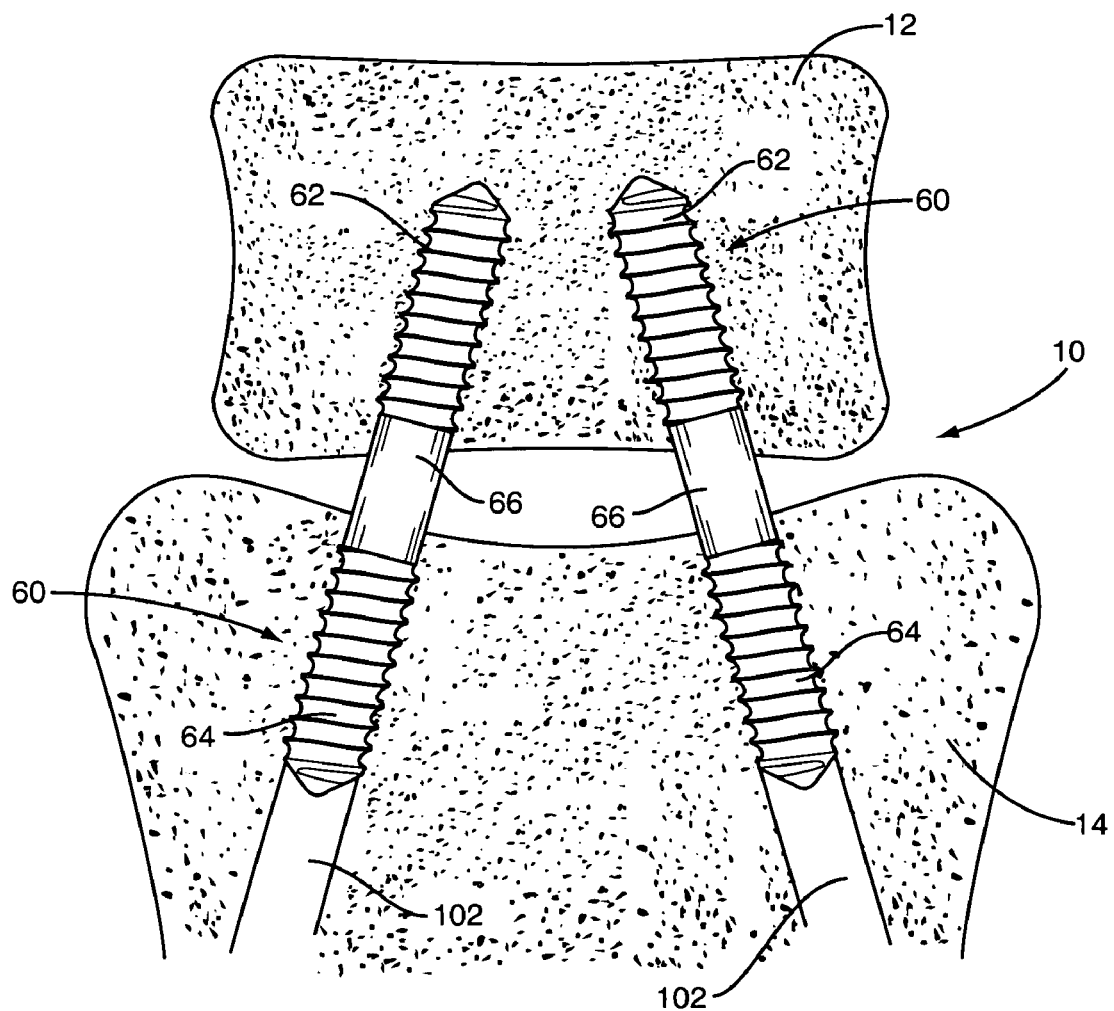
FIG. 13 illustrates a sixth exemplary embodiment of the intervertebral joint.

FIG. 13 illustrates a sixth embodiment of the intervertebral joint 10. This embodiment comprises a double-ended shaft 60 having a first threaded end portion 62 for insertion into the lumbar vertebra 12, and a second threaded end portion 64 for insertion into the sacral 14. The end portions 62, 64 are connected by a flexible midsection 66. The end sections 62, 64 may be made of titanium, cobalt chrome, plastic, or bioabsorbable material. The flexible midsection 66 is made of a flexible material such as silicon and polycarbonate urethane. In the embodiment shown in FIG. 11, two double-ended shafts 60 are used to form an intervertebral joint 10. Approach holes 102, 104 are formed in the sacral 14 through which the double-ended shafts 60 are inserted. The double-ended shafts 60 are threaded into the lumbar vertebra 12 such that the flexible midsections 66 are disposed in the space between the lumbar vertebra 12 and sacrum 14.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An orthopedic device comprising:
    a socket screw having a shaft for insertion into a first bone and a ball socket positioned at the end of the shaft; and
    a ball screw for insertion into a second bone, the ball screw including a shaft having a longitudinal axis and a rounded head fixed on the shaft and adapted to engage with the ball socket to form a ball joint, the rounded head being offset from the longitudinal axis of the shaft;
    a first support screw having an elongated shape with a first end and a second end, the support screw including a length configured for the first end to be mounted into the first bone with the second end configured to extend outward from the first bone to contact an outer surface of the ball socket at a point away from the shaft of the socket screw; and
    a second support screw having a shaft to be mounted into the second bone and an end that contacts against the rounded head of the ball screw.

2. The orthopedic device of claim 1 wherein the ball socket is disposed at an angle relative to a longitudinal axis of the socket screw.

3. The orthopedic device of claim 2 wherein the angle is within a range of 35 to 55 degrees.

4. The orthopedic device of claim 1 wherein the first support screw includes a concave surface in one end thereof to engage the socket screw.

5. The orthopedic device of claim 1 wherein the end of the second support screw is rounded for contacting the ball screw.

6. The orthopedic device of claim 1 wherein the end of the second support screw has a concave surface for contacting the ball screw.

7. A method of forming an artificial joint between first and second bones comprising:
    inserting a socket screw including a ball socket into a first bone;
    inserting a first support screw into the first bone to engage and support the ball socket at a point away from the socket screw; and
    inserting a ball screw including a rounded head that is fixed to a shaft into a second bone such that the rounded head engages in said ball socket to form a ball joint;
    wherein the first and second bones comprise vertebral members; further comprising inserting the socket screw through an approach hole formed in the second bone.

8. The method of claim 7 wherein the ball screw threads into and plugs the approach hole.

9. The method of claim 7 wherein the first bone is a lumbar vertebra and wherein the second bone is a sacrum.

10. The method of claim 7 further comprising inserting a second support screw into the second bone to engage and support the ball screw.

11. The method of claim 7 further comprising rotating the ball screw and causing the rounded head that is offset to intermittently contact the socket screw.

\* \* \* \* \*